US 6,617,475 B2

(12) United States Patent
Studer et al.

(10) Patent No.: US 6,617,475 B2
(45) Date of Patent: Sep. 9, 2003

(54) PREPARATION OF OPTICALLY ACTIVE α-HYDROXYETHERS

(75) Inventors: Martin Studer, Basel (CH); Stephan Burkhardt, Gelterkinden (CH)

(73) Assignee: Solvias AG, Basel (CH)

( * ) Notice: Subject to any disclaimer, the term of this patent is extended or adjusted under 35 U.S.C. 154(b) by 0 days.

(21) Appl. No.: 10/233,441

(22) Filed: Sep. 4, 2002

(65) Prior Publication Data

US 2003/0109712 A1 Jun. 12, 2003

(30) Foreign Application Priority Data

Sep. 5, 2001 (CH) ............................................. 1648/01

(51) Int. Cl.$^7$ ............................................. C07C 41/26
(52) U.S. Cl. ........................ 568/648; 568/660; 568/670; 568/678
(58) Field of Search ................................ 568/648, 660, 568/670, 678

(56) References Cited

U.S. PATENT DOCUMENTS 3,818,013 A * 6/1974 Yardley et al. ............. 546/134
4,329,487 A * 5/1982 Orito et al. ................... 560/60
5,066,801 A * 11/1991 Blaser et al. ................ 540/523
6,417,389 B1 * 7/2002 Studer et al. ................. 560/53

FOREIGN PATENT DOCUMENTS

JP 62158268 * 7/1987 ......... C07D/307/32

OTHER PUBLICATIONS

Studer et al., Hydrogenation of alpha–keto ether . . . heterogeneous base, Advanced Synthesis & Catalysis, Jul. 2002, vol. 344, No. 5, pp. 511–515.*

* cited by examiner

Primary Examiner—Rosalynd Keys
(74) Attorney, Agent, or Firm—Wenderoth, Lind & Ponack, L.L.P.

(57) ABSTRACT

Optically active α-hydroxyethers are prepared from prochiral α-ketoethers by heterogeneous hydrogenation using platinum catalysts in the presence of a chiral nitrogen base in high chemical and optical yields, since this type of hydrogenation selectively hydrogenates only one diastereomer virtually to completion. The yields may be substantially increased by adding a solid, strong base which has a racemizing effect on the non-hydrogenatable diasteromer.

18 Claims, No Drawings

PREPARATION OF OPTICALLY ACTIVE α-HYDROXYETHERS

The present invention relates to a process for heterogeneously, asymmetrically hydrogenating racemic α-ketoethers using a platinum catalyst in the presence of a chiral aromatic nitrogen base and optionally a strong base to give enantiomeric α-hydroxyethers.

Optically active α-hydroxyethers are valuable intermediates for preparing tricyclic β-lactam antibiotics (Matsumoto, T. et al. THL 40 (1999) 5043) and natural compounds (Murata, K., et al., Org. Lett. 1 (1999) 1119), active pharmaceutical ingredients and pesticides. As early as 1979, Y. Orito et al. in Nippon Kagaku Kuishi 1979(8), pages 1118–1120 disclose that optically active α-hydroxycarboxylic esters are obtainable in good optical yields by hydrogenating α-ketocarboxylic esters using platinum metal catalysts in the presence of a cinchona alkaloid. The influence of solvents and other reaction conditions in this hydrogenation is described by H. U. Blaser et al. in J. of Mol. Cat. 68 (1991), pages 215 to 222. Further investigations have shown (see H. U. Blaser et al. in Catalysis Today 37 (1997), pages 441 to 461) that the catalytic hydrogenation system has a high substrate specificity. Even the use of α-diketones instead of the α-ketocarboxylic esters (optical yield ee up to 95%) leads to considerably reduced optical yields (ee only 38 to 50%, see also W. A. H. Vermeer et al. in J. Chem. Soc., Chem. Comm., 1993, pages 1053 to 1054 and M. Studer et al. in J. Chem. Soc., Chem. Comm., 1998, page 1053). When an unsubstituted methyl α-ketoether such as methoxyacetone is used, the effect is even more pronounced and an optical yield of only about 12% ee is obtained (H. U. Blaser et al. in Heterogeneous Catalysis and Fine Chemicals, Elsevier Science Publishers B. V., Amsterdam, 1998, pages 153 to 163). WO 01/00545 discloses that, in contrast, α-ketoacetals in this hydrogenation deliver excellent chemical and optical yields.

The targeted preparation of substituted enantiomeric α-hydroxyethers from prochiral α-ketoethers by heterogeneous hydrogenation using platinum catalysts in the presence of a chiral nitrogen base has hitherto not been described. It has now been found that, surprisingly, this type of hydrogenation selectively hydrogenates only one diastereomer to virtual completion and accordingly very high chemical and optical yields are achievable, especially because the reactants and adducts are easily separable owing to their differing physical properties.

It is known that α-ketoethers can be racemized using soluble strong bases. Although soluble bases accelerate the reaction, they lead to a completely racemized product. It was found that, surprisingly, the yield of the desired diastereomer could be greatly increased when a strong heterogeneous base was added to the reaction mixture. During the hydrogenation, the undesired diastereomer is racemized and the desired diastereomer is formed and hydrogenated. In this manner, the chemical yield can be greatly increased to over 90% and more.

The invention accordingly provides a process for heterogeneously and enantioselectively hydrogenating organic α-keto compounds using a platinum catalyst in the presence of a soluble or immobilized chiral aromatic nitrogen base having at least one basic nitrogen atom neighbouring at least one stereogenic carbon atom, which is characterized in that racemic α-ketoethers are hydrogenated to optically active α-hydroxyethers.

Neighbouring stereogenic carbon atoms means that the nitrogen atom is not bonded to the stereogenic carbon atom, but instead that the basic nitrogen atom is in the β- and more preferably in the α-position to at least one stereogenic carbon atom.

The racemic α-ketoethers may be saturated or unsaturated, open-chain or cyclic compounds which preferably have 5 to 50, more preferably 5 to 30, carbon atoms and are unsubstituted or substituted by one or more radicals which are stable under the hydrogenation conditions. The carbon chain may be interrupted by heteroatoms, preferably from the group of —O—, =N— and —NR'— and/or —C(O)—, —C(NR')—, —C(O)—O—, —C(O)—NR'— where R' is H, $C_1$–$C_8$-alkyl, $C_5$- or $C_6$-cycloalkyl or $C_6$–$C_{10}$-aryl, for example phenyl or naphthyl, or phenylmethyl or phenylethyl.

Examples of useful inert substituents include alkyl, alkenyl, alkoxy, haloalkyl, hydroxyalkyl, alkoxyalkyl, haloalkoxy, cycloalkyl, cycloalkoxy, cycloalkylalkyl, cycloalkylalkoxy, aryl, aryloxy, aralkyl, aralkoxy, halogen, —OH, —OR$_4$, —OC(O)R$_4$, —NH—C(O)—R$_4$, —NR$_4$—C(O)—R$_4$, —CO$_2$R$_4$, —CO$_2$—NH$_2$, —CO$_2$—NHR$_4$, and —CO$_2$—NR$_4$R$_5$ where R$_4$ and R$_5$ are each independently $C_1$–$C_4$-alkyl, cyclohexyl, cyclohexylmethyl, phenyl or benzyl.

The α-ketoethers are preferably of the formula I,

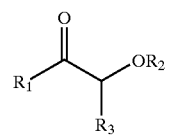

(I)

where R$_1$, R$_2$ and R$_3$ are each independently a monovalent, saturated or unsaturated aliphatic radical having 1 to 12 carbon atoms, a saturated or unsaturated cycloaliphatic radical having 3 to 8 carbon atoms, a saturated or unsaturated heterocycloaliphatic radical having 3 to 8 ring members and one or two heteroatoms from the group of O, N and NR', a saturated or unsaturated cycloaliphatic-aliphatic radical having 4 to 12 carbon atoms, a saturated or unsaturated heterocycloaliphatic-aliphatic radical having 3 to 12 carbon atoms and one or two heteroatoms from the group of O, N and NR', an aromatic radical having 6 to 10 carbon atoms, a heteroaromatic radical having 4 to 9 carbon atoms and one or two heteroatoms from the group of O and N, an aromatic-aliphatic radical having 7 to 12 carbon atoms or a heteroaromatic-aliphatic radical having 5 to 11 carbon atoms and one or two heteroatoms from the group of O and N where R' is H, $C_1$–$C_8$-alkyl, preferably $C_1$–$C_4$-alkyl, $C_5$- or $C_6$-cycloalkyl or $C_6$–$C_{10}$-aryl, for example phenyl or naphthyl, phenyl or phenylethyl, R$_1$ and R$_2$ together or R$_1$ and R$_3$ together form a direct bond, $C_1$–$C_6$-alkylene, $C_3$–$C_8$-cycloalkyl-1,2-ene, $C_3$–$C_8$-cycloalkyl-$C_1$–$C_4$-alkylene, $C_2$–$C_7$-heterocycloalkyl-1,2-ene or $C_2$–$C_7$-heterocycloalkyl-$C_1$–$C_4$-alkylene having one or two heteroatoms from the group of O and N, $C_6$–$C_{10}$-aryl-$C_1$–$C_4$-alkylene, $C_5$–$C_9$-heteroaryl-$C_1$–$C_4$-alkylene having one or two heteroatoms from the group of O and N; or $C_2$–$C_{10}$-alkylene, $C_3$–$C_8$-cycloalkylene or $C_2$–$C_7$-heterocycloalkylene having one or two heteroatoms from the group of O and N, each of which is fused to $C_3$–$C_8$-cycloalkyl-1,2-ene, $C_2$–$C_7$-heterocycloalkyl-1,2-ene having one or two heteroatoms from the group of O and N, $C_6$–$C_{10}$-aryl-1,2-ene or $C_5$–$C_9$-heteroaryl-1,2-ene having one or two heteroatoms from the group of O and N, and $R_3$ and $R_2$ respectively are each as defined above, $R_2$ and $R_3$ together are $C_1$–$C_6$-alkylene, $C_1$–$C_8$-alkylidene, $C_3$–$C_8$-cycloalkylidene, benzylidene, $C_3$–$C_8$-cycloalkyl-1,2-ene, $C_3$–$C_8$-cycloalkyl-$C_1$–$C_4$-alkylene, $C_2$–$C_7$-heterocycloalkyl-1,2-ene or $C_2$–$C_7$-heterocycloalkyl-$C_1$–$C_4$-alkylene having one or two heteroatoms from the group of O and N, $C_6$–$C_{10}$-aryl-$C_1$–$C_4$-alkylene, $C_5$–$C_9$-heteroaryl-$C_1$–$C_4$-alkylene having one or two heteroatoms from the group of O and N; or $C_2$–$C_{10}$-alkylene, $C_3$–$C_8$-cycloalkylene or $C_2$–$C_7$-heterocycloalkylene having one or two heteroatoms from the group of O and N, each of which is fused to $C_3$–$C_8$-cycloalkyl-1,2-ene, $C_2$–$C_7$-heterocycloalkyl-1,2-ene having one or two heteroatoms from the group of O and N, $C_6$–$C_{10}$-aryl-1,2-ene or $C_5$–$C_9$-heteroaryl-1,2-ene having one or two heteroatoms from the group of O and N, and $R_1$ is as defined above, and $R_1$, $R_2$ and $R_3$ are each unsubstituted or substituted by one or more, identical or different radicals selected from the group of $C_1$–$C_4$-alkyl, $C_2$–$C_4$-alkenyl, $C_1$–$C_4$-alkoxy, $C_1$–$C_4$-haloalkyl, $C_1$–$C_4$-hydroxyalkyl, $C_1$–$C_4$-alkoxymethyl or -ethyl, $C_1$–$C_4$-haloalkoxy, cyclohexyl, cyclohexyloxy, cyclohexylmethyl, cyclohexylmethyloxy, phenyl, phenyloxy, benzyl, benzyloxy, phenylethyl, phenylethyloxy, halogen, —OH, —OR$_4$, —OC(O)R$_4$, —NH$_2$, —NHR$_4$, —NR$_4$R$_5$, —NH—C(O)—R$_4$, —NR$_4$—C(O)—R$_4$, —CO$_2$R$_4$, —CO$_2$—NH$_2$, —CO$_2$—NHR$_4$, —CO$_2$—NR$_4$R$_5$, where $R_4$ and $R_5$ are each independently $C_1$–$C_4$-alkyl, cyclohexyl, cyclohexylmethyl, phenyl or benzyl.

The heterocyclic radicals are bonded via a ring carbon atom to the oxygen atom or the carbon atom of the carbonyl group in formula I.

Preferred substituents include methyl, ethyl, n- and i-propyl, n- and t-butyl, vinyl, allyl, methyloxy, ethyloxy, n- and i-propyloxy, n- and t-butyloxy, trifluoromethyl, trichloromethyl, β-hydroxyethyl, methoxy- or ethoxymethyl or -ethyl, trifluoromethoxy, cyclohexyl, cyclohexyloxy, cyclohexylmethyl, cyclohexylmethyloxy, phenyl, phenyloxy, benzyl, benzyloxy, phenylethyloxy, phenylethyl, halogen, —OH, —OR$_4$, —OC(O)R$_4$, —NH$_2$, —NHR$_4$, —NR$_4$R$_5$, —NH—C(O)—R$_4$, —NR$_4$—C(O)—R$_4$, —CO$_2$R$_4$, —CO$_2$—NH$_2$, —CO$_2$—NHR$_4$, —CO$_2$—NR$_4$R$_5$ where $R_4$ and $R_5$ are each independently $C_1$–$C_4$-alkyl, cyclohexyl, cyclohexylmethyl, phenyl or benzyl.

The aliphatic radical is preferably alkyl which may be linear or branched and preferably contains 1 to 8, more preferably 1 to 4, carbon atoms, or preferably alkenyl or alkynyl which may be linear or branched and preferably contains 2 to 8, more preferably 2 to 4, carbon atoms. When $R_2$ and $R_3$ are alkenyl or alkynyl, the unsaturated bond is preferably in the β-position to the oxygen atom. Examples include methyl, ethyl, n- and i-propyl, n-, i- and t-butyl, pentyl, i-pentyl, hexyl, heptyl, octyl, nonyl, decyl, undecyl and dodecyl, vinyl, allyl, ethynyl and propargyl. A preferred group of aliphatic radicals consists of methyl, ethyl, n- and i-propyl, n-, i- and t-butyl.

The cycloaliphatic radical is preferably cycloalkyl or cycloalkenyl having preferably from 3 to 8, more preferably 5 or 6, ring carbon atoms. Examples include cyclopropyl, cyclobutyl, cyclopentyl, cyclohexyl, cycloheptyl and cyclooctyl, and also cyclopentenyl, cyclohexenyl and cyclohexadienyl. Particular preference is given to cyclopentyl and cyclohexyl.

The heterocycloaliphatic radical is preferably heterocycloalkyl or heterocycloalkenyl preferably having 3 to 6 carbon atoms, 4 to 7 ring members and heteroatoms selected from the group of —O— and —NR'— where R' is H, $C_1$–$C_8$-alkyl, preferably $C_1$–$C_4$-alkyl, $C_5$- or $C_6$-cycloalkyl or $C_6$–$C_{10}$-aryl, for example phenyl or naphthyl, phenyl or phenylethyl. Examples include pyrrolidinyl, pyrrolinyl, tetrahydrofuranyl, dihydrofuranyl and piperazinyl.

The cycloaliphatic-aliphatic radical is preferably cycloalkyl-alkyl or -alkenyl preferably having 3 to 8, more preferably 5 or 6, ring carbon atoms, and preferably 1 to 4 or 2–4, more preferably 1 or 2, or 2 or 3, carbon atoms in the alkyl group or alkenyl group respectively. Examples include cyclopentyl- or cyclohexylmethyl or -ethyl and cyclopentyl- or cyclohexylethenyl.

The heterocycloaliphatic-aliphatic radical is preferably heterocycloalkyl-alkyl or -alkenyl preferably having 3 to 6 carbon atoms, 4 to 7 ring members and heteroatoms selected from the group of —O— and —NR'— where R' is H, $C_1$–$C_8$-alkyl, preferably $C_1$–$C_4$-alkyl, $C_5$- or $C_6$-cycloalkyl or $C_6$–$C_{10}$-aryl, for example phenyl or naphthyl, phenyl or phenylethyl, and preferably 1 to 4, more preferably 1 or 2, carbon atoms in the alkyl group or 2 to 4, and more preferably 2 or 3, carbon atoms in the alkenyl group. Examples include pyrrolidinylmethyl or -ethyl or -ethenyl, pyrrolinylmethyl or -ethyl or -ethenyl, tetrahydrofuranylmethyl or -ethyl or -ethenyl, dihydrofuranylmethyl or -ethyl or -ethenyl, and piperazinylmethyl or -ethyl or -ethenyl.

The aromatic radicals are particularly naphthyl and in particular phenyl.

The aromatic-aliphatic radicals are preferably phenyl- or naphthyl-$C_1$–$C_4$-alkyl or —$C_2$–$C_4$-alkenyl. Examples include benzyl, naphthylmethyl, β-phenylethyl and β-phenylethenyl.

The heteroaromatic radicals are preferably 5- or 6-membered, optionally fused, ring systems. Examples include pyridinyl, pyrimidinyl, pyrazinyl, pyrrolyl, furanyl, oxazolyl, imidazolyl, benzofuranyl, indolyl, benzimidazolyl, quinolinyl, isoquinolinyl, quinazolinyl and quinoxalinyl.

The heteroaromatic-aliphatic radicals are preferably 5- or 6-membered, optionally fused, ring systems which are bonded via one of their carbon atoms to the free bond of an alkyl group which preferably has 1 to 4, more preferably 1 or 2, carbon atoms, or of an alkenyl group which preferably has 2 to 4, more preferably 2 or 3, carbon atoms. Examples include pyridinylmethyl or -ethyl or -ethenyl, pyrimidinylmethyl or -ethyl or -ethenyl, pyrrolylmethyl or -ethyl or -ethenyl, furanylmethyl or -ethyl or -ethenyl, imidazolylmethyl or -ethyl or -ethenyl, indolylmethyl or -ethyl or -ethenyl.

More preferred compounds of the formula I include those where

R$_1$, R$_2$ and R$_3$ are each independently linear or branched C$_1$–C$_8$-alkyl, C$_4$–C$_7$-cycloalkyl or C$_4$–C$_6$-heterocycloalkyl having heteroatoms from the group of O and N, C$_6$–C$_{10}$-aryl or C$_4$–C$_9$-heteroaryl having heteroatoms from the group of O and N, C$_4$–C$_7$-cycloalkyl-C$_1$–C$_4$-alkyl or C$_3$–C$_6$-heterocycloalkyl-C$_1$–C$_4$-alkyl having heteroatoms from the group of O and N, C$_6$–C$_{10}$-aryl-C$_1$–C$_4$-alkyl or C$_4$–C$_9$-heteroaryl-C$_1$–C$_4$-alkyl having heteroatoms from the group of O and N, R$_1$ and R$_2$ together or R$_1$ and R$_3$ together are each C$_1$–C$_4$-alkylene or C$_4$–C$_7$-1,2-cycloalkylene, or C$_2$–C$_4$-alkylene or C$_4$–C$_7$-cycloalkylene fused to 1,2-phenylene, and R$_3$ or R$_2$ respectively are each as defined above, R$_2$ and R$_3$ together are C$_1$–C$_4$-alkylene, C$_1$–C$_4$-alkylidene, C$_4$–C$_7$-1,2-cycloalkylene, C$_4$–C$_7$-cycloalkylidene, benzylidene, 1,2-phenylene, 1,2-pyridinylene or 1,2-naphthylene, or C$_3$–C$_4$-alkylene or C$_4$–C$_7$-cycloalkylene fused to 1,2-cycloalkylene or to 1,2-phenylene, and R$_1$ is as defined above, where R$_1$, R$_2$ and R$_3$ are each unsubstituted or substituted by one or more, identical or different radicals selected from the group of C$_1$–C$_4$-alkyl, C$_1$–C$_4$-alkoxy, C$_1$–C$_4$-haloalkyl, C$_1$–C$_4$-hydroxyalkyl, C$_1$–C$_4$-alkoxymethyl or -ethyl, C$_1$–C$_4$-haloalkoxy, cyclohexyl, cyclohexyloxy, cyclohexylmethyl, cyclohexylmethyloxy, phenyl, phenyloxy, benzyl, benzyloxy, phenylethyl, phenylethyloxy, halogen, —OH, —OR$_4$, —OC(O)R$_4$, —NH$_2$, —NHR$_4$, —NR$_4$R$_5$, —NH—C(O)—R$_4$, —NR$_4$—C(O)—R$_4$, —CO$_2$R$_4$, —CO$_2$—NH$_2$, —CO$_2$-NHR$_4$ and —CO$_2$—NR$_4$R$_5$ where R$_4$ and R$_5$ are each independently C$_1$–C$_4$-alkyl, cyclohexyl, phenyl or benzyl.

A preferred subgroup of the compounds of the formula I includes those where

R$_1$, R$_2$ and R$_3$ are each independently linear or branched C$_1$–C$_4$-alkyl, C$_2$–C$_4$-alkenyl, C$_5$–C$_6$-cycloalkyl, phenyl, phenylethenyl, C$_5$–C$_6$-cycloalkyl-C$_1$–C$_2$-alkyl or C$_6$–C$_{10}$-aryl-C$_1$–C$_2$-alkyl, R$_1$ and R$_2$ together or R$_1$ and R$_3$ together are C$_1$–C$_3$-alkylene or C$_5$–C$_6$-1,2-cycloalkylene, R$_2$ and R$_3$ together are C$_2$–C$_4$-alkylene, C$_1$–C$_4$-alkylidene, C$_5$–C$_6$-1,2-cycloalkylene, C$_5$–C$_6$-cycloalkylidene, benzylidene or 1,2-phenylene, where R$_1$, R$_2$ and R$_3$ are each unsubstituted or substituted as defined above.

A particularly preferred subgroup of the compounds of the formula I includes those where R$_1$ is C$_1$–C$_4$-alkyl, C$_2$–C$_4$-alkenyl, cyclohexyl, phenyl, benzyl, phenylethyl or phenylethenyl, R$_2$ and R$_3$ are each independently linear or branched C$_1$–C$_4$-alkyl, cyclohexyl, phenyl, benzyl or phenylethyl, R$_1$ and R$_2$ together or R$_1$ and R$_3$ together are each C$_2$–C$_3$-alkylene or 1,2-cyclohexylene, R$_2$ and R$_3$ together are C$_2$–C$_3$-alkylene, C$_1$–C$_4$-alkylidene, 1,2-cyclohexylene, cyclohexylidene, benzylidene or 1,2-phenylene, where R$_1$, R$_2$ and R$_3$ are each unsubstituted or substituted by methyl, ethyl, n- and i-propyl, n- and t-butyl, vinyl, allyl, methyloxy, ethyloxy, n- and i-propyloxy, n- and t-butyloxy, trifluoromethyl, trichloromethyl, β-hydroxyethyl, methoxy- or ethoxymethyl or -ethyl, trifluoromethoxy, cyclohexyl, cyclohexyloxy, cyclohexylmethyl, cyclohexylmethyloxy, phenyl, phenyloxy, benzyl, benzyloxy, phenylethyloxy, phenylethyl, halogen, —OH, —OR$_4$, —OC(O)R$_4$, —NH$_2$, —NHR$_4$, —NR$_4$R$_5$, —NH—C(O)—R$_4$, —NR$_4$—C(O)—R$_4$, —CO$_2$R$_4$, —CO$_2$—NH$_2$, —CO$_2$—NHR$_4$ or —CO$_2$—NR$_4$R$_5$ where R$_4$ and R$_5$ are each independently C$_1$–C$_4$-alkyl, cyclohexyl, cyclohexylmethyl, phenyl or benzyl.

α-Ketoethers are known or may be prepared in a conventional manner by the literature processes.

The α-ketoethers, in particular those of the formula I, are hydrogenated to chiral secondary alcohols of the formula II

(II)

where R$_1$, R$_2$ and R$_3$ are each as defined above and the symbol * represents predominantly the R- or S-form of one of the stereoisomers.

Platininum catalysts are known, extensively described and commercially available. Platinum can easily be used in metallic form, for example as powder, or else, preferably, as platinum metal applied to a finely divided support. Examples of useful supports include carbon, metal oxides, for example SiO$_2$, TiO$_2$ or Al$_2$O$_3$, metal salts, and natural or synthetic silicates. The catalyst may also be a platinum colloid. The quantity of platinum metal on the support may be, for example 1 to 10, preferably 3 to 8, % by weight, based on the support. Before use, the catalysts may be activated by treatment with hydrogen at elevated temperature or using ultrasound.

Chiral and aromatic nitrogen bases as modifiers for platinum-catalyzed enantioselective hydrogenation are likewise known and described, for example, by H. U. Blaser et al. in Catalysis Today 37 (1997), pages 441 to 463. Particularly useful nitrogen bases have an aromatic or heteroaromatic, mono- or polycyclic, ring system, preferably a mono- to tricyclic ring, optionally in combination with fused-on cycloaliphatic or heterocycloaliphatic rings, and the basic nitrogen atom or atoms are bonded in the α- and preferably in the β-position to a chiral carbon atom and the nitrogen atoms are ring members of a chiral N-heterocyclo-aliphatic ring or are bonded to a ring via a chiral C$_1$- or C$_2$-group.

Preference is given to cinchona alkaloids and derivatives thereof. They may, for example, be of the formula III

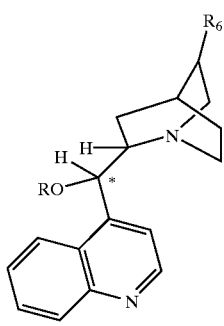
(III)

where R is H, $C_1$–$C_4$-alkyl, $C_1$–$C_4$-alkyl-C(O)—, $C_1$–$C_4$-hydroxyalkyl-C(O)—, phenyl-C(O)— or benzyl-C(O)—, $R_6$ is H, $C_1$–$C_4$-alkyl, $C_1$–$C_4$-hydroxyalkyl or $C_2$–$C_4$-alkenyl, and the symbol * represents the R- or S-form of the stereocentres. Preference is given to cinchona alkaloids where $R_6$ in the formula III is H, methyl, ethyl or vinyl, and R is H, methyl, ethyl or acetyl.

The choice of the nitrogen base predetermines which of the enantiomeric α-hydroxyethers is formed predominantly.

The catalyst (for example 5% of $Pt/Al_2O_3$) may be used, for example in a quantity of 0.01 to 10, preferably 0.05 to 50 and more preferably 0.1 to 10, % by weight, based on the α-ketoether used, although quantities of 0.1 to 5% by weight, or 0.1 to 1% by weight generally suffice.

The nitrogen base is added, for example, in a quantity of from 0.1 to 1 000, preferably 1 to 500 and more preferably 10 to 200, % by weight, based on the platinum metal catalyst used. The nitrogen base may be added together with the platinum metal catalyst into the reaction vessel, or the platinum catalyst may be impregnated with the nitrogen base, for example a cinchona alkaloid, in a preceding step.

Preference is given to carrying out the hydrogenation under a hydrogen pressure of up to 200 bar, more preferably up to 150 bar and particularly preferably 10 to 100 bar.

The reaction temperature may be, for example –50 to 100° C., more preferably 0 to 50° C. and particularly preferably 0 to 35° C.

The reaction may be carried out without or in an inert solvent. Examples of useful solvents include aliphatic, cycloaliphatic and aromatic hydrocarbons (pentane, hexane, petroleum ether, cyclohexane, methylcyclohexane, benzene, toluene or xylene), ethers (diethyl ether, dibutyl ether, ethylene glycol dimethyl ether, ethylene glycol diethyl ether, diethylene glycol dimethyl ether, tetrahydrofuran or dioxane), alcohols (methanol, ethanol, propanol, butanol, ethylene glycol, diethylene glycol, ethylene glycol monomethyl or monoethyl ether or diethylene glycol monomethyl or monoethyl ether), ketones (acetone or methyl isobutyl ketone), carboxylic esters and lactones (ethyl acetate or methyl acetate, valerolactone), N-substituted carboxamides and lactams (dimethylformamide or N-methylpyrrolidone) and carboxylic acids (acetic acid, propionic acid or butyric acid). The optical yield may be influenced by the choice of solvent.

It has proven particularly advantageous to carry out the process according to the invention in the presence of at least one strong base in solid form which is insoluble in the reaction mixture. The base is used advantageously in finely divided form (powder). The term insoluble also includes bases which can be swollen in the reaction system. These bases may in particular be those strong bases which are able to deprotonate the chiral CH group of the α-ketoethers in order to racemize the non-hydrogenatable diastereomers. Preference is given to bases having $OH^-$ groups, for example alkali metal hydroxides and in particular optionally crosslinked homo- or copolymers having ammonium hydroxide groups or inorganic supports modified with ammonium hydroxide groups. Among the polymeric ammonium hydroxides, preference is given to those based on optionally crosslinked polyaminostyrenes. These strong bases are familiar as anion exchangers and are commercially available. Examples include the amberlites (Amberlite® IRA-900) from Fluka AG, a crosslinked copolymer or styreneammonium chloride and divinylbenzene which is activated using aqueous alkali before use. Inorganic supports, for example glass, metal oxides, silica gel or silicates, may be modified, for example, using aminoalkyltrialkoxysilanes and then converted using ammonia salts such as halides by treatment with bases to the ammonium hydroxide form. The quantity of the solid base may be, for example from 1 to 100, preferably from 10 to 90 and more preferably from 20 to 80, % by weight, based on the α-ketoether.

The process according to the invention may be carried out in such a manner that, for example, the catalyst is initially charged with the chiral nitrogen base into an autoclave, optionally with a solvent, then the α-ketoether is added, air is expelled using an inert gas, for example noble gases or hydrogen, hydrogen is injected, and the reaction is started, optionally with stirring or shaking, and hydrogenation is effected until such time as no more hydrogen takeup is observed. The α-hydroxyether formed may be isolated and purified by customary methods, for example distillation, crystallization and chromatographic methods. The process according to the invention provides the desired α-hydroxyethers in high chemical and optical yields, and high catalyst activity is additionally observed so that even the use of small catalyst quantities provides an economical process. Furthermore, insoluble strong bases are successfully used for the first time in a dynamic, kinetic optical resolution in a heterogeneous reaction system in order to achieve higher yields of the desired diastereomers.

The examples hereinbelow illustrate the invention. The conversion is determined by means of $^1$H-NMR.

EXAMPLES 1–6

Hydrogenation of 2-Methoxycyclohexanone 5 mg of methoxyhydrocinchonidine are initially charged into a 50 ml pressure autoclave equipped with a magnetic stirrer and baffles. 50 mg of platinum catalyst (JMC 94, Batch 14017/01, Johnson Matthey, pretreated under hydrogen over 2 h at 400° C.) are slurried in 2 ml of glacial acetic acid and transferred to the autoclave. 1 g of 2-methoxycyclohexanone (7.8 mmol) is dissolved in the remainder of the solvent (total 20 ml) and likewise transferred to the autoclave. The autoclave is purged 3 times with argon and 3 times with hydrogen and then hydrogen is injected to 60 bar. The reaction is started by switching on the magnetic stirrer. The temperature is held at a constant 25° C. with the aid of a cryostat. The pressure in the autoclave is held constant during the reaction using a dome pressure regulator and the hydrogen uptake in the reactor is measured by the pressure drop in a reservoir. After the end of the reaction, the autoclave is depressurized, purged 3 times with argon and opened. The catalyst is filtered off and the reaction mixture concentrated to dryness. Yield: 0.86 g ($C_7H_{14}O_2$, MW 130, 19 g, 6.61 mmol, 85%). Chromatography: Carlo Erba GC 6000, Vega Series II, β-Dex 100 column based on β-cyclodextrin, 30 m, 0.25 mm internal diameter, Supelco 24301, T=85° C. (isothermal), $H_2$ carrier gas, 120 kPa, $T_{inj}$ 220° C., $T_{Det}$ 250° C. Retention times for reactants 10.0 min (the two enantiomers are not separated), 10.80 and 10.98 min for the two cis enantiomers, and 11.80 and 12.09 min for the two trans enantiomers.

and 100 mg of catalyst are used. In addition, 7 mg of KOH are added. The yield is 0.75 g of product of 90% purity containing 10% solvent (88%).

EXAMPLE 6

Hydrogenation of 2-Methoxycyclohexanone

Example 1 is repeated, except that 2 g of reactant, toluene as solvent, 20 mg of hydrocinchonidine as modifier and 200 mg of catalyst are used. In addition, 1.6 g of Amberlite® IRA-900 are added. The yield is 1.96 g of product of 80% purity containing 20% of solvent (78%).

The results of Examples 1 to 6 are summarized in Table 1. Abbreviations in the tables: Me is methyl and n.d. is not determined. Rate is the reaction rate in mmol/min*g.

TABLE 1

| 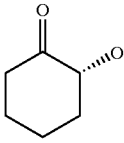 | | 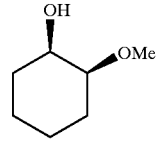 | | 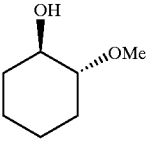 | | | |
|---|---|---|---|---|---|---|---|
| Content | ee | Content | ee | Content | ee | Rate | Example |
| 41% | n.d. | 58% | 76% | 1% | n.d. | 13.7 | 1 |
| 44% | n.d. | 55% | 78% | 1% | n.d. | 2.4 | 2 |
| 17% | n.d. | 79% | 27% | 3% | 91% | 0.8 | 3 |
| 0% | n.d. | 97% | 56% | 3% | 27% | 1.7 | 4 |
| 0% | n.d. | 78% | 1% | 22% | 1% | 22.7 | 5 |
| 2% | n.d. | 97% | 82% | 1% | n.d. | 3.1 | 6 |

EXAMPLE 2

Hydrogenation of 2-Methoxycyclohexanone

Example 1 was repeated, except that toluene was used as solvent and hydrocinchonidine as modifier. The yield was 0.73 g (72%).

EXAMPLE 3

Hydrogenation of 2-Methoxycyclohexanone

Example 1 is repeated, except that isopropanol is used as solvent, 10 mg of hydrocinchonidine are used as modifier and 100 mg of catalyst are used. The yield is 0.6 g of product of 70% purity containing 30% solvent (54%).

EXAMPLE 4

Hydrogenation of 2-Methoxycyclohexanone

Example 1 is repeated, except that isopropanol is used as solvent, 10 mg of hydrocinchonidine are used as modifier and 100 mg of catalyst are used. In addition, 800 mg of Amberlite IRA-900 (strongly basic anion exchanger, activated using NaOH) are added. The yield is 0.36 g of product of 95% purity containing 5% solvent (44%).

EXAMPLE 5

Hydrogenation of 2-Methoxycyclohexanone

Example 1 is repeated, except that isopropanol is used as solvent, 10 mg of hydrocinchonidine are used as modifier

EXAMPLE 7

Hydrogenation of 2-Benzoin Methyl Ether 10 mg of hydrocinchonidine are initially charged into a 50 ml pressure autoclave equipped with a magnetic stirrer and baffles. 100 mg of catalyst (JMC 94, Batch 14017/01, Johnson Matthey, pretreated under hydrogen over 2 h at 400° C.) are slurried in 2 ml of glacial acetic acid and transferred to the autoclave. 1 g of benzoin methyl ether is dissolved in the remainder of the solvent (total 20 ml) and likewise transferred to the autoclave. The autoclave is purged 3 times with argon and 3 times with hydrogen and then hydrogen is injected to 60 bar. The reaction is started by switching on the magnetic stirrer. The temperature is held at a constant 25° C. with the aid of a cryostat. The pressure in the autoclave is held constant during the reaction using a dome pressure regulator and the hydrogen uptake in the reactor is measured by the pressure drop in a reservoir. After the end of the reaction, the autoclave is depressurized, purged 3 times with argon and opened. The catalyst is filtered off and the reaction mixture concentrated to dryness. Yield: 0.65 g (64%). Chromatography: HP 1100 HPLC, Chiracel® OD (Daicel) 0.46×25 cm, isocratic hexane/isopropanol (98:2). Detection at 210 nm. Retention times 12.6 and 21.3 min for the reactant, 25.5 and 31.9 min for the two syn-enantiomers, and 16.4 and 19.5 min for the two anti-enantiomers.

EXAMPLE 8

Hydrogenation of 2-Benzoin Methyl Ether

Example 7 is repeated, except that toluene is used as solvent.

EXAMPLE 9

Hydrogenation of 2-Benzoin Methyl Ether

Example 7 is repeated, except that 2 g of reactant are used and toluene is used as solvent. In addition, 1.6 g of Amberlite® IRA-900 are added.

The results of Examples 7 to 9 are summarized in Table 2.

autoclave is held constant during the reaction using a dome pressure regulator and the hydrogen uptake in the reactor is measured by the pressure drop in a reservoir. After the end of the reaction, the autoclave is depressurized, purged 3 times with argon and opened. The catalyst is filtered off and the reaction mixture analysed. The yield was not determined owing to the volatility of the product. Chromatography: Carlo Erba GC 6000, Vega Series II, β-Dex 100 column based on β-cyclodextrin, 30 m, 0.25 mm internal diameter, Supelco 24301. $H_2$ carrier gas, 120 kPa, $T_{inj}$ 220° C., $T_{Det}$ 250° C. T=50° C. (10 min), then 2° C./min. The retention times are 4.9 and 5.1 min for the reactant, 10.5 and 10.8 min for the two syn-enantiomers, and 7.8 and 8.0 min for the two anti-enantiomers.

TABLE 2

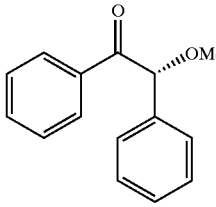

| Content | ee | Content | ee | Content | ee | Rate | Example |
|---|---|---|---|---|---|---|---|
| 61% | 28% | 34% | 56% | 4% | 8% | 0.7 | 7 |
| 46% | 65% | 52% | 88% | 2% | 75% | 0.2 | 8 |
| 8% | 7% | 90% | 90% | 2% | 36% | 0.9 | 9 |

EXAMPLE 10

Hydrogenation of 2-Methoxybutanone 10 mg of hydrocinchonidine are initially charged into a 50 ml pressure autoclave equipped with a magnetic stirrer and baffles. 100 mg of catalyst (JMC 94, Batch 14017/01, Johnson Matthey, pretreated under hydrogen over 2 h at 400° C.) are slurried in 2 ml of glacial acetic acid and transferred to the autoclave. 0.7 g of 2-methoxybutanone ($C_5H_{10}O_2$, MW 102.13, 6.85 mmol) is dissolved in the remainder of the solvent (total 20 ml) and likewise transferred to the autoclave. The autoclave is purged 3 times with argon and 3 times with hydrogen and then hydrogen is injected to 100 bar. The reaction is started by switching on the magnetic stirrer. The temperature is held at a constant 25° C. with the aid of a cryostat. The pressure in the

EXAMPLE 11

Hydrogenation of 2-Methoxybutanone

Example 10 is repeated, except that benzene is used as solvent.

The results of Examples 10 and 11 are summarized in Table 3.

TABLE 3

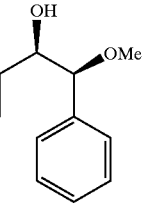

| Content | ee | Content | ee | Content | ee | Rate | Example |
|---|---|---|---|---|---|---|---|
| 58% | 78% | 32% | 95% | 2% | n.d. | 2.4 | 10[1] |
| 45% | 78% | 45% | 79% | 7% | n.d. | 2.4 | 10[1] |
| 81% | 4% | 11% | 45% | 7% | 20% | 0.2 | 11[1] |

[1]Samples for measurement withdrawn after 39, 226 and 463 minutes respectively.

EXAMPLE 12

Hydrogenation of 2-Benzyloxybutanone 10 mg of hydrocinchonidine are initially charged into a 50 ml pressure autoclave equipped with a magnetic stirrer and baffles. 100 mg of catalyst (JMC 94, Batch 14017/01, Johnson Matthey, pretreated under hydrogen over 2 h at 400° C.) are slurried in 2 ml of toluene and transferred to the autoclave. 0.7 g of 2-benzyloxybutanone (5.62 mmol) is dissolved in the remainder of the solvent (total 20 ml) and likewise transferred to the autoclave. The autoclave is purged 3 times with argon and 3 times with hydrogen and then hydrogen is injected to 100 bar. The reaction is started by switching on the magnetic stirrer. The temperature is held at a constant 25° C. with the aid of a cryostat. The pressure in the autoclave is held constant during the reaction using a dome pressure regulator and the hydrogen uptake in the reactor is measured by the pressure drop in a reservoir. After the end of the reaction, the autoclave is depressurized, purged 3 times with argon and opened. The catalyst is filtered off and the reaction mixture concentrated to dryness. Yield: 0.88 g (87%). Chromatography: Carlo Erba GC 6000, Vega Series II, β-Dex 100 column based on β-cyclodextrin, 30 m, 0.25 mm internal diameter, Supelco 24301. $H_2$ carrier gas, 120 kPa, $T_{inj}$ 220° C., $T_{Det}$ 250° C. T=120° C., isothermal. Retention times for the reactant 14.9 and 15.2 min. Product not separated, an HPLC system has to be used. Identification of syn/anti is ambiguous. HP 1100 HPLC. Chiracel® OD (Daicel) 0.46×25 cm, isocratic hexane/isopropanol (98:2). Detection at 210 nm. Retention times 16.8 and 19.4 min for the two syn-enantiomers, and 13.7 and 14.1 min for the two anti-enantiomers (no base line separation).

EXAMPLE 13

Hydrogenation of 2-Benzyloxybutanone

Example 10 is repeated, except that glacial acetic acid is used as solvent. Yield: 1.19 g (about 100%, still contains about 20% of glacial acetic acid).

The results of Examples 12 and 13 are summarized in Table 4.

conditions, and the carbon chain may optionally be interrupted by heteroatoms from the group of —O—, =N— and —NR'— and/or —C(O)—, —C(NR')—, —C(O)—O—, —C(O)—NR'— where R' is H, $C_1$–$C_8$-alkyl, $C_5$- or $C_6$-cycloalkyl or $C_6$–$C_{10}$-aryl.

3. Process according to claim 1, characterized in that the α-ketoethers are of the formula I,

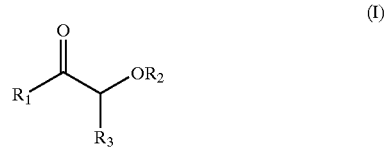

(I)

where $R_1$, $R_2$ and $R_3$ are each independently a monovalent, saturated or unsaturated aliphatic radical having 1 to 12 carbon atoms, a saturated or unsaturated cycloaliphatic radical having 3 to 8 carbon atoms, a saturated or unsaturated heterocycloaliphatic radical having 3 to 8 ring members and one or two heteroatoms from the group of O, N and NR', a saturated or unsaturated cycloaliphatic-aliphatic radical having 4 to 12 carbon atoms, a saturated or unsaturated heterocycloaliphatic-aliphatic radical having 3 to 12 carbon atoms and one or two heteroatoms from the group of O, N and NR', an aromatic radical having 6 to 10 carbon atoms, a heteroaromatic radical having 4 to 9 carbon atoms and one or two heteroatoms from the group of O and N, an aromatic-aliphatic radical having 7 to 12 carbon atoms or a heteroaromatic-aliphatic radical having 5 to 11 carbon atoms and one or two heteroatoms from the group of O and N where R' is H, $C_1$–$C_8$-alkyl, $C_5$- or $C_6$-cycloalkyl or $C_6$–$C_{10}$-aryl, $R_1$ and $R_2$ together or $R_1$ and $R_3$ together form a direct bond, $C_1$–$C_6$-alkylene, $C_3$–$C_6$-cycloalkyl-1,2-ene, $C_3$–$C_6$-cycloalkyl-$C_1$–$C_4$-alkylene, $C_2$–$C_7$-heterocycloalkyl-1,2-ene or $C_2$–$C_7$-heterocycloalkyl-$C_1$–$C_4$-alkylene having one or two heteroatoms from

TABLE 4

| Content | ee | Content | ee | Content | ee | Rate | Example |
|---|---|---|---|---|---|---|---|
| 93% | 4% | 5% | 75% | 2% | n.d. | 0.2 | 12[1) |
| 79% | 12% | 13% | 68% | 8% | n.d. | 2.4 | 12[1) |
| 82% | 16% | 16% | 77% | 3% | about 20% | 0.3 | 13[2) |
| 67% | 28% | 27% | 66% | 6% | about 30% | 0.3 | 13[2) |

[1)Samples for measurement taken after 83 and 386 minutes respectively.
[2)Samples for measurement taken after 53 and 153 minutes respectively.

What is claimed is:

1. Process for heterogeneously and enantioselectively hydrogenating organic α-keto compounds using a platinum catalyst in the presence of a soluble or immobilized chiral aromatic nitrogen base having at least one basic nitrogen atom neighbouring at least one stereogenic carbon atom, characterized in that racemic α-ketoethers are hydrogenated to optically active α-hydroxyethers.

2. Process according to claim 1, characterized in that the racemic α-ketoethers are saturated or unsaturated, open-chain or cyclic compounds which contain 5 to 50 carbon atoms and are unsubstituted or substituted by one or more radicals which are stable under the hydrogenation the group of O and N, $C_6$–$C_{10}$-aryl-$C_1$–$C_4$-alkylene, $C_5$–$C_9$-heteroaryl-$C_1$–$C_4$-alkylene having one or two heteroatoms from the group of O and N; or $C_2$–$C_{10}$-alkylene, $C_3$–$C_8$-cycloalkylene or $C_2$–$C_7$-heterocycloalkylene having one or two heteroatoms from the group of O and N, each of which is fused to $C_3$–$C_8$-cycloalkyl-1,2-ene, $C_2$–$C_7$-heterocycloalkyl-1, 2-ene having one or two heteroatoms from the group of O and N, $C_6$–$C_{10}$-aryl-1,2-ene or $C_5$–$C_9$-heteroaryl-1, 2-ene having one or two heteroatoms from the group of O and N, and $R_3$ and $R_2$ respectively are each as defined above, $R_2$ and $R_3$ together are $C_1$–$C_6$-alkylene, $C_1$–$C_8$-alkylidene, $C_3$–$C_8$-cycloalkylidene, benzylidene, $C_3$–$C_8$-cycloalkyl-1,2-ene, $C_3$–$C_8$-cycloalkyl-$C_1$–$C_4$-alkylene, $C_2$–$C_7$-heterocycloalkyl-1,2-ene or $C_2$–$C_7$-heterocycloalkyl-$C_1$–$C_4$-alkylene having one or two heteroatoms from the group of O and N, $C_6$–$C_{10}$-aryl-$C_1$–$C_4$-alkylene, $C_5$–$C_9$-heteroaryl-$C_1$–$C_4$-alkylene having one or two heteroatoms from the group of O and N; or $C_2$–$C_{10}$-alkylene, $C_3$–$C_8$-cycloalkylene or $C_2$–$C_7$-heterocycloalkylene having one or two heteroatoms from the group of O and N, each of which is fused to $C_3$–$C_8$-cycloalkyl-1,2-ene, $C_2$–$C_7$-heterocycloalkyl-1,2-ene having one or two heteroatoms from the group of O and N, $C_6$–$C_{10}$-aryl-1,2-ene or $C_5$–$C_9$-heteroaryl-1,2-ene having one or two heteroatoms from the group of O and N, and $R_1$ is as defined above, and $R_1$, $R_2$ and $R_3$ are each unsubstituted or substituted by one or more, identical or different radicals selected from the group of $C_1$–$C_4$-alkyl, $C_2$–$C_4$-alkenyl, $C_1$–$C_4$-alkoxy, $C_1$–$C_4$-haloalkyl, $C_1$–$C_4$-hydroxyalkyl, $C_1$–$C_4$-alkoxymethyl or -ethyl, $C_1$–$C_4$-haloalkoxy, cyclohexyl, cyclohexyloxy, cyclohexylmethyl, cyclohexylmethyloxy, phenyl, phenyloxy, benzyl, benzyloxy, phenylethyl, phenylethyloxy, halogen, —OH, —$OR_4$, —$OC(O)R_4$, —$NH_2$, —$NHR_4$, —$NR_4R_5$, —NH—C(O)—$R_4$, —$NR_4$—C(O)—$R_4$, —$CO_2R_4$, —$CO_2$—$NH_2$, —$CO_2$—$NHR_4$, —$CO_2$—$NR_4R$, where $R_4$ and $R_5$ are each independently $C_1$–$C_4$-alkyl, cyclohexyl, cyclohexylmethyl, phenyl or benzyl.

4. Process according to claim 1, characterized in that the catalyst is present as a metal, a metal colloid or as a metal applied to a finely divided support material.

5. Process according to claim 4, characterized in that the support material is $Al_2O_3$.

6. Process according to claim 1, characterized in that the catalyst is used in a quantity of 0.01 to 10% by weight, based on the α-ketoether.

7. Process according to claim 1, characterized in that the chiral nitrogen base is a cinchona alkaloid or a derivative thereof.

8. Process according to claim 7, characterized in that the chiral nitrogen base is a compound of the formula III

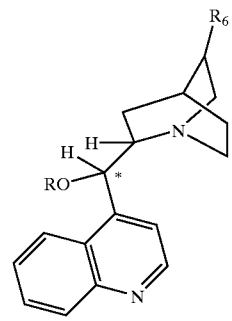

(III)

where R is H, $C_1$–$C_4$-alkyl, $C_1$–$C_4$-alkyl-C(O)—, $C_1$–$C_4$-hydroxyalkyl-C(O)—, phenyl-C(O)— or benzyl-C(O)—, $R_6$ is H, $C_1$–$C_4$-alkyl, $C_1$–$C_4$-hydroxyalkyl or $C_2$–$C_4$-alkenyl, and the symbol * represents the R- or S-form of the stereocentres.

9. Process according to claim 8, characterized in that $R_6$ in the formula III is H, methyl, ethyl or vinyl, and R is H, methyl, ethyl or acetyl.

10. Process according to claim 1, characterized in that the nitrogen base is used in a quantity of from 0.1 to 1000% by weight, based on the platinum catalyst.

11. Process according to claim 1, characterized in that it is carried out in an inert solvent.

12. Process according to claim 1, characterized in that at least one solid and strong base which is insoluble in the reaction mixture is additionally present.

13. Process according to claim 12, characterized in that the base is able to deprotonate the chiral CH group of the α-ketoethers.

14. Process according to claim 12, characterized in that the bases are hydroxide groups.

15. Process according to claim 14, characterized in that the bases are alkali metal hydroxides or optionally crosslinked homo- or copolymers having ammonium hydroxide groups or inorganic supports modified with ammonium hydroxide groups.

16. Process according to claim 14, characterized in that the polymeric ammonium hydroxide is based on optionally crosslinked polyaminostyrene.

17. Process according to claim 12, characterized in that the quantity of base is 1 to 100 percent by weight, based on the α-ketoether.

18. Process according to claim 3, wherein R' is $C_1$–$C_4$-alkyl, phenyl, naphthyl or phenylethyl.

* * * * *